US011940578B2

United States Patent
Tavitian et al.

(10) Patent No.: US 11,940,578 B2
(45) Date of Patent: Mar. 26, 2024

(54) SUPER RESOLUTION IN POSITRON EMISSION TOMOGRAPHY IMAGING USING ULTRAFAST ULTRASOUND IMAGING

(71) Applicants: INSERM (Institut National de la Santé et de la Recherche Médicale), Paris (FR); Université de Paris, Paris (FR); Centre National de la Recherche Scientifique (CNRS), Paris (FR); Ecole Supérieure de Physique et de Chimie Industrielles de la Ville de Paris, Paris (FR)

(72) Inventors: Bertrand Tavitian, Paris (FR); Mickaël Tanter, Paris (FR); Mailyn Perez-Liva, Paris (FR); Joaquin Lopez Herraiz, Madrid (ES); Jean Provost, Montreal (CA)

(73) Assignees: INSERM (INSTITUT NATIONAL DE LA SANTÉ ET DE LA RECHERCHE MÉDICALE), Paris (FR); UNIVERSITÉ DE PARIS, Paris (FR); CENTRE NATIONAL DE LA RECHERCHE SCIENTIFIQUE—CNRS, Paris (FR); ECOLE SUPERIEURE DE PHYSIQUE ET DE CHIMIE INDUSTRIELLES DE LA VILLE DE PARIS, Paris (FR)

( * ) Notice: Subject to any disclaimer, the term of this patent is extended or adjusted under 35 U.S.C. 154(b) by 555 days.

(21) Appl. No.: 17/160,866

(22) Filed: Jan. 28, 2021

(65) Prior Publication Data
US 2021/0239863 A1 Aug. 5, 2021

(30) Foreign Application Priority Data

Jan. 31, 2020 (EP) .................................... 20154857

(51) Int. Cl.
*G01T 1/29* (2006.01)
*A61B 6/00* (2006.01)

(52) U.S. Cl.
CPC .......... *G01T 1/2985* (2013.01); *A61B 6/5229* (2013.01); *A61B 6/5235* (2013.01)

(58) Field of Classification Search
CPC .... G01T 1/2985; A61B 6/5229; A61B 6/5235
See application file for complete search history.

(56) References Cited

PUBLICATIONS

Schwaab et al., "First steps Toward Ultrasound-Based Motion compensation for imaging and Therapy: calibration with an Optical system and 4D PET imaging", 2015, Front. Oncol. 5:258. doi: 10.3389/fonc.2015.00258, pp. 1-10 (10 pages) (Year: 2015).*

(Continued)

*Primary Examiner* — David F Dunphy
(74) *Attorney, Agent, or Firm* — WCF IP

(57) ABSTRACT

An imaging method including:
a) acquiring N successive positron emission tomography (PET) low resolution images $\Gamma_i$ and simultaneously, N successive Ultrafast Ultrasound Imaging (UUI) images Ui of a moving object;
b) determining from each UUI image Ui, the motion vector fields $M_i$ that corresponds to the spatio-temporal geometrical transformation of the motion of the object;
c) obtaining a final estimated high resolution image H of the object by iterative determination of a high resolution image $H^{n+1}$ obtained by applying several correction iterations to a current estimated high resolution image $H^n$, n being the number of iterations, starting from an initial estimated high resolution image $H^1$ of the object, each correction iteration including at least:
i) warping the estimated high resolution image $H^n$ using the motion vector fields $M_i$ to determine a set of low resolution reference images $L''_i$;
ii) determining a differential image Di by difference between each PET image $\Gamma_i$ and the corresponding low resolution reference image $L''_i$;
iii) warping back the differential images Di using the motion vector fields $M_i$ and averaging the N warped back differential images to obtain a high resolution differential image;
iv) determining the high resolution image $H^{n+1}$ by correcting the high resolution image $H^n$ using the high resolution differential image;

(Continued)

d) applying the motion vector fields $M_i$ of each UUI image Ui to the final high resolution image H.

20 Claims, 3 Drawing Sheets

(56) References Cited

PUBLICATIONS

Provost et al., "Simultaneous positron emission tomography and ultrafast ultrasound for hybrid molecular, anatomical and functional imaging," 2018, Nature Biomedical Engineering, 2018, 2, pp. 85-94 (13 pages) (Year: 2018).*
European Search Report; dated May 19, 2020.
Kennedy et al.; "Super Resolution in PET Imaging"; IEEE Transaction on Medical Imaging, vol. 25, No. 2, Feb. 2006, pp. 137-147.
Perez-Liva et al.; "Super resolustion in preclinical cardiac PET using ultrafast ultrasound imaging"; 14th European Molecular Imaging Meeting, Conference Abstracts, Mar. 29, 2019, the whole document.
Provost et al.; "Simultaneous prositron emission tomography and ultrafast ultrasound for hybrid molecular, anatomical and functional imaging"; Nature Biomedical Engineering, vol. 2, No. 2, Feb. 6, 2018, pp. 85-94.

* cited by examiner

SUPER RESOLUTION IN POSITRON EMISSION TOMOGRAPHY IMAGING USING ULTRAFAST ULTRASOUND IMAGING

FIELD

The disclosure relates to imaging methods, devices and computer-readable mediums for improving the image-quality of positron emission tomography (PET).

BACKGROUND

Standing as a paradox with respect to the vast number of applications in oncology and neurology, cardiac metabolic imaging using 2-deoxy-2-[$^{18}$F]fluoro-D-glucose (FDG) positron emission tomography (PET) has so far found few clinical applications. One reason is the difficulty to attribute changes in FDG cardiac uptake to pathological versus physiological causes, e.g. substrate availability, energetic demand, neural and hormonal regulation [1, 2].

Under basal conditions, the energetic metabolism of the normal adult heart is mostly supported by the oxidation of fatty acids. Other substrates such as lactate, ketone bodies and glucose, contribute minorly [2]. However, in conditions of increased cardiac energy demand, both physiological, e.g. strenuous exercise, or pathophysiological, e.g. acute ischemia, myocarditis, left ventricle hypertrophy, systemic hypertension, drug toxicity, there is a switch towards glycolysis and, just as in the fetal heart, glucose becomes the preferred source of fuel of the adult heart [3-6].

PET imaging of the heart in rodent models would facilitate the exploration of the connection between the level of glucose metabolism and cardiac (patho)physiology.

However, high-quality imaging of the rodent heart remains a technical challenge because of the gap between the dimensions of the heart's movements, i.e. left-ventricle displacement-velocity of around 2-3 cm/s [7-10] at 300-800 beats per minute [11], and the spatial and temporal resolutions of preclinical PET scanners, over 1 mm [12] and seconds to minutes, respectively [7]; while the human heart beats at more than one Hertz and the left ventricle displacement velocity reaches 1-16 cm/s [25].

Therefore, each cardiac PET image accumulates several heart cycles, leading to significant blurring, motion-induced artifacts, and imprecise radioactivity quantification. Gating raw PET data along the cardiac cycles synchronously with an electrocardiogram (ECG) compensates for cardiac motion (Gated Cardiac-PET [13]), but comes at the cost of lower counting statistics and contrast.

A number of methods, collectively termed Super-Resolution (SR), have been proposed to improve the spatial resolution of PET [14-21]. SR is based on iterative inverse algorithms that use a priori information from an anatomical reference in order to (i) characterize the motion vector fields (MVF) of the heart's motion and (ii) increase spatial sampling through shifts with sub-resolution precision [15, 22, 23].

Gated Cardiac-PET frames are readily available priors for SR but they are far from ideal due to their high noise content and low resolution [15, 23], and most SR methods use a second imaging modality, such as X-ray tomography (CT) or magnetic resonance imaging (MRI).

The inventors recently proposed a non-invasive, in-vivo, preclinical imaging instrument, PETRUS [9, 24], that merges simultaneously acquired PET-Computed Tomography (PET-CT) and Ultrafast Ultrasound Imaging (UUI).

However, so far, ultrasound has not been used as anatomical reference for SR correction in rodent cardiac PET imaging.

In the present disclosure, an ultrasound-based SR method has been evaluated, using simultaneously acquired and co-registered PET-CT and Ultrafast Ultrasound Imaging (UUI) of the beating heart in closed-chest rodents.

Bibliography (references in the present disclosure are made according to the following numbering):

[1] J. Jeppesen and B. Kiens, "Regulation and limitations to fatty acid oxidation during exercise," J. Physiol. (Lond.), vol. 590, (5), pp. 1059-1068, 2012.

[2] F. Pascual and R. A. Coleman, "Fuel availability and fate in cardiac metabolism: A tale of two substrates," Biochimica Et Biophysica Acta (BBA)-Molecular and Cell Biology of Lipids, vol. 1861, (10), pp. 1425-1433, 2016.

[3] J. Sourdon, F. Lager, T. Viel, D. Balvay, R. Moorhouse, E. Bennana, G. Renault, P. L. Tharaux, N. Dhaun and B. Tavitian, "Cardiac Metabolic Deregulation Induced by the Tyrosine Kinase Receptor Inhibitor Sunitinib is rescued by Endothelin Receptor Antagonism," Theranostics, vol. 7, (11), pp. 2757-2774, Jul. 8, 2017.

[4] F. Haas, L. Jennen, U. Heinzmann, N. Augustin, M. Wottke, M. Schwaiger and R. Lange, "Ischemically compromised myocardium displays different time-courses of functional recovery: correlation with morphological alterations?" European Journal of Cardio-Thoracic Surgery, vol. 20, (2), pp. 290-298, 2001.

[5] M. R. Vesely and V. Dilsizian, "Nuclear cardiac stress testing in the era of molecular medicine," J. Nucl. Med., vol. 49, (3), pp. 399-413, March, 2008.

[6] L. Hernández-Esquivel, A. Marín-Hernández, N. Pavón, K. Carvajal and R. Moreno-Sánchez, "Cardiotoxicity of copper-based antineoplastic drugs casiopeinas is related to inhibition of energy metabolism," Toxicol. Appl. Pharmacol., vol. 212, (1), pp. 79-88, 2006.

[7] W. W. Moses, "Fundamental limits of spatial resolution in PET," Nuclear Instruments and Methods in Physics Research Section A: Accelerators, Spectrometers, Detectors and Associated Equipment, vol. 648, pp. S236-S240, 2011.

[8] J. Luo and E. E. Konofagou, "Imaging of wall motion coupled with blood flow velocity in the heart and vessels in vivo: a feasibility study," Ultrasound Med. Biol., vol. 37, (6), pp. 980-995, 2011.

[9] M. Perez-Liva, T. Viel, T. Yoganathan, A. Garofalakis, J. Sourdon, C. Facchin, M. Tanter, J. Provost and B. Tavitian, "Performance evaluation of the PET component of a hybrid PET/CT-ultrafast ultrasound imaging instrument," Physics in Medicine & Biology, vol. 63, (19), pp. 19NT01, 2018.

[10] E. P. Visser, J. A. Disselhorst, M. Brom, P. Laverman, M. Gotthardt, W. J. Oyen and O. C. Boerman, "Spatial resolution and sensitivity of the Inveon small-animal PET scanner," J. Nucl. Med., vol. 50, (1), pp. 139-147, January, 2009.

[11] Website: "Animal Care and Use Johns Hopkins University," [online] http://web.jhu.edu/animalcare/procedures/mouse.html. Accessed on Dec. 10, 2019.

[12] W. P. Segars, B. M. Tsui, E. C. Frey, G. A. Johnson and S. S. Berr, "Development of a 4-D digital mouse phantom for molecular imaging research," Molecular Imaging & Biology, vol. 6, (3), pp. 149-159, 2004.

[13] N. Lang, M. Dawood, F. Büther, O. Schober, M. Schäfers and K. Schäfers, "Organ movement reduction in

[14] A. Marquina and S. J. Osher, "Image super-resolution by TV-regularization and Bregman iteration," J. Sci. Comput., vol. 37, (3), pp. 367-382, 2008.

[15] I. J. Ahn, J. H. Kim, Y. Chang, W. H. Nam and J. B. Ra, "Super-resolution reconstruction of 3d pet images using two respiratory-phase low-dose ct images," IEEE Transactions on Radiation and Plasma Medical Sciences, vol. 1, (1), pp. 46-55, 2016.

[16] J. A. Kennedy, O. Israel, A. Frenkel, R. Bar-Shalom and H. Azhari, "Super-resolution in PET imaging," IEEE Trans. Med. Imaging, vol. 25, (2), pp. 137-147, 2006.

[17] S. Ambwani, W. C. Karl, A. Tawakol and H. Pien, "Joint cardiac and respiratory motion correction and super-resolution reconstruction in coronary PET/CT," in 2011 IEEE International Symposium on Biomedical Imaging: From Nano to Macro, 2011, pp. 1702-1705.

[18] J. L. Rubio-Guivernau, M. J. Ledesma-Carbayo, F. Lamare, J. E. Ortuno, P. Guerra, D. Visvikis, A. Santos and G. Kontaxakis, "Respiratory motion correction in PET with super-resolution techniques and non-rigid registration," in 2007 IEEE Nuclear Science Symposium Conference Record, 2007, pp. 3560-3563.

[19] H. Yan, F. Gigengack, X. Jiang and K. Schäfers, "Super-resolution in cardiac PET using mass-preserving image registration," in 2013 IEEE International Conference on Image Processing, 2013, pp. 752-756.

[20] J. A. Kennedy, O. Israel, A. Frenkel, R. Bar-Shalom and H. Azhari, "Super-resolution in PET imaging," IEEE Trans. Med. Imaging, vol. 25, (2), pp. 137-147, 2006.

[21] D. Wallach, F. Lamare, G. Kontaxakis and D. Visvikis, "Super-resolution in respiratory synchronized positron emission tomography," IEEE Trans. Med. Imaging, vol. 31, (2), pp. 438-448, 2011.

[22] T. Küstner, M. Schwartz, P. Martirosian, S. Gatidis, F. Seith, C. Gilliam, T. Blu, H. Fayad, D. Visvikis and F. Schick, "MR-based respiratory and cardiac motion correction for PET imaging," Med. Image Anal., vol. 42, pp. 129-144, 2017.

[23] W. H. Nam, I. J. Ahn, K. M. Kim, B. I. Kim and J. B. Ra, "Motion-compensated PET image reconstruction with respiratory-matched attenuation correction using two low-dose inhale and exhale CT images," Physics in Medicine & Biology, vol. 58, (20), pp. 7355, 2013.

[24] J. Provost, A. Garofalakis, J. Sourdon, D. Bouda, B. Berthon, T. Viel, M. Perez-Liva, C. Lussey-Lepoutre, J. Favier and M. Correia, "Simultaneous positron emission tomography and ultrafast ultrasound for hybrid molecular, anatomical and functional imaging," Nature Biomedical Engineering, vol. 2, (2), pp. 85, 2018.

[25] H. Poorzand, A. Sadeghpour, A. Alizadehasl and S. Saha, "Echocardiographic assessment of myocardial mechanics: Velocity, strain, strain rate and torsion," in Case-Based Textbook of EchocardiographyAnonymous Springer, 2018, pp. 141-167

[26] A. Tristán-Vega, G. Vegas-Sánchez-Ferrero and S. Aja-Fernández, "Local similarity measures for demons-like registration algorithms," in 2008 5th IEEE International Symposium on Biomedical Imaging: From Nano to Macro, 2008, pp. 1087-1090.

[27] J. Thirion, "Image matching as a diffusion process: an analogy with Maxwell's demons," Med. Image Anal., vol. 2, (3), pp. 243-260, 1998.

[28] M. Felsberg and G. Sommer, "The monogenic signal," IEEE Transactions on Signal Processing, vol. 49, (12), pp. 3136-3144, 2001.

[29] M. Mellor and M. Brady, "Phase mutual information as a similarity measure for registration," Med. Image Anal., vol. 9, (4), pp. 330-343, 2005.

[30] C. P. Bridge, "Introduction to the monogenic signal," arXiv Preprint arXiv:1703.09199, 2017.

[31] J. Cal-González, M. Pérez-Liva, J. L. Herraiz, J. J. Vaquero, M. Desco and J. M. Udias, "Tissue-dependent and spatially-variant positron range correction in 3D PET," Medical Imaging, IEEE Transactions On, vol. 34, (11), pp. 2394-2403, 2015.

[32] A. Badal, J. Domarco, J. M. Udias and J. L. Herraiz, "MCGPU-PET: A real-time monte carlo PET simulator," in International Symposium on Biomedical Imaging, Washington, D.C., 2018.

[33] J. Herraiz, S. España, R. Cabido, A. Montemayor, M. Desco, J. J. Vaquero and J. M. Udías, "GPU-based fast iterative reconstruction of fully 3-D PET sinograms," IEEE Trans. Nucl. Sci., vol. 58, (5), pp. 2257-2263, 2011.

[34] E. Peli, "Contrast in complex images," Josa A, vol. 7, (10), pp. 2032-2040, 1990.

[35] N. B. Schiller, "Two-dimensional echocardiographic determination of left ventricular volume, systolic function, and mass. Summary and discussion of the 1989 recommendations of the American Society of Echocardiography," Circulation, vol. 84, (3 Suppl), pp. 1280-7, September, 1991.

[36] J. Provost, A. Garofalakis, J. Sourdon, D. Bouda, B. Berthon, T. Viel, M. Perez-Liva, C. Lussey-Lepoutre, J. Favier and M. Correia, "Simultaneous positron emission tomography and ultrafast ultrasound for hybrid molecular, anatomical and functional imaging," Nature Biomedical Engineering, vol. 2, (2), pp. 85, 2018.

[37] D. Wallach, F. Lamare, C. Roux and D. Visvikis, "Comparison between reconstruction-incorporated super-resolution and super-resolution as a post-processing step for motion correction in PET," in IEEE Nuclear Science Symposium & Medical Imaging Conference, 2010, pp. 2294-2297.

[38] Q. Huang and Z. Zeng, "A review on real-time 3D ultrasound imaging technology," BioMed Research International, vol. 2017, 2017.

SUMMARY OF THE DISCLOSURE

The scope of the disclosure is defined by the claims. Any subject-matter falling outside the scope of the claims is provided for information purposes only.

It is hereby disclosed an ultrasound-based Super-Resolution (SR) method using simultaneously acquired and co-registered Positron Emission Tomography-Computed Tomography (PET-CT) and Ultrafast Ultrasound Imaging (UUI) of the beating heart in closed-chest rodents. The method was tested with numerical and animal data (n=2) acquired with the non-invasive in vivo preclinical imaging system PETRUS [9, 24], that fuses PET, CT and UUI.

Cardiac PETRUS allows the acquisition, during the same imaging session, of glucose metabolism and real-time high resolution cardiac motion with negligible effects on PET image quality [9]. This Ultrasound-based SR method was applied in the image domain and its performance was tested on simulated and real preclinical datasets.

The results show that the Ultrasound-based SR technique disclosed herein, based on co-registered, simultaneously acquired PET and ultrasonic data, enhances the quality of metabolic PET images of the beating rodent heart in terms of spatial resolution, signal-to-noise ratio (SNR) and contrast.

Results obtained show that, when compared to static PET, image contrast is improved by a factor of two, SNR by 40% and spatial resolution by 56% (~0.88 mm). As a consequence, the metabolic defect following an acute cardiac ischemia was delineated with higher anatomical precision.

The performance of the method was demonstrated using numerical and animal data. In the infarcted rat heart, the method disclosed herein improved the delineation of the metabolic defect due to the post-ischemic lesion. PET-UUI data with the SR technique disclosed herein allows improved imaging of cardiac metabolism, moreover in pathological situations such as ones characterized by cardiac glucose dysregulation.

Therefore, an imaging method, an imaging device and a computer-readable medium are provided, that improve the image quality of the corrected images in terms of contrast and/or signal-to-noise ratio (SNR) and/or spatial resolution, compared to static PET.

LIST OF ABBREVIATIONS

Abbreviations used in the present disclosure refers to the following terms:
ECG=Electrocardiogram
FDG=[18F]Fluoro-2-deoxy-2-D-glucose
FWHM=Full-Width-at-Half-Maximum
LADCA=Left Anterior Descending Coronary Artery
MEAN=Mean Value
MVF=Motion Vector Fields
PET=Positron Emission Tomography
PET-CT=Positron Emission Tomography-Computed Tomograph
PSF=Point Spread Function
RMSE=Root-Mean-Square-Error
ROI=Regions Of Interest
SNR=signal-to-noise ratio
SR=Super-Resolution
STD=Standard Deviation
SUV=Standard Uptake Value
TV=Total Variation
UUI=Ultrafast Ultrasound Imaging

BRIEF DESCRIPTION OF DRAWINGS

Other features and advantages of the disclosure appear from the following detailed description of one non-limiting example thereof, with reference to the accompanying drawings.

In the drawings.

DETAILED DESCRIPTION

A. Super-Resolution in the Image Domain

Figure 1:
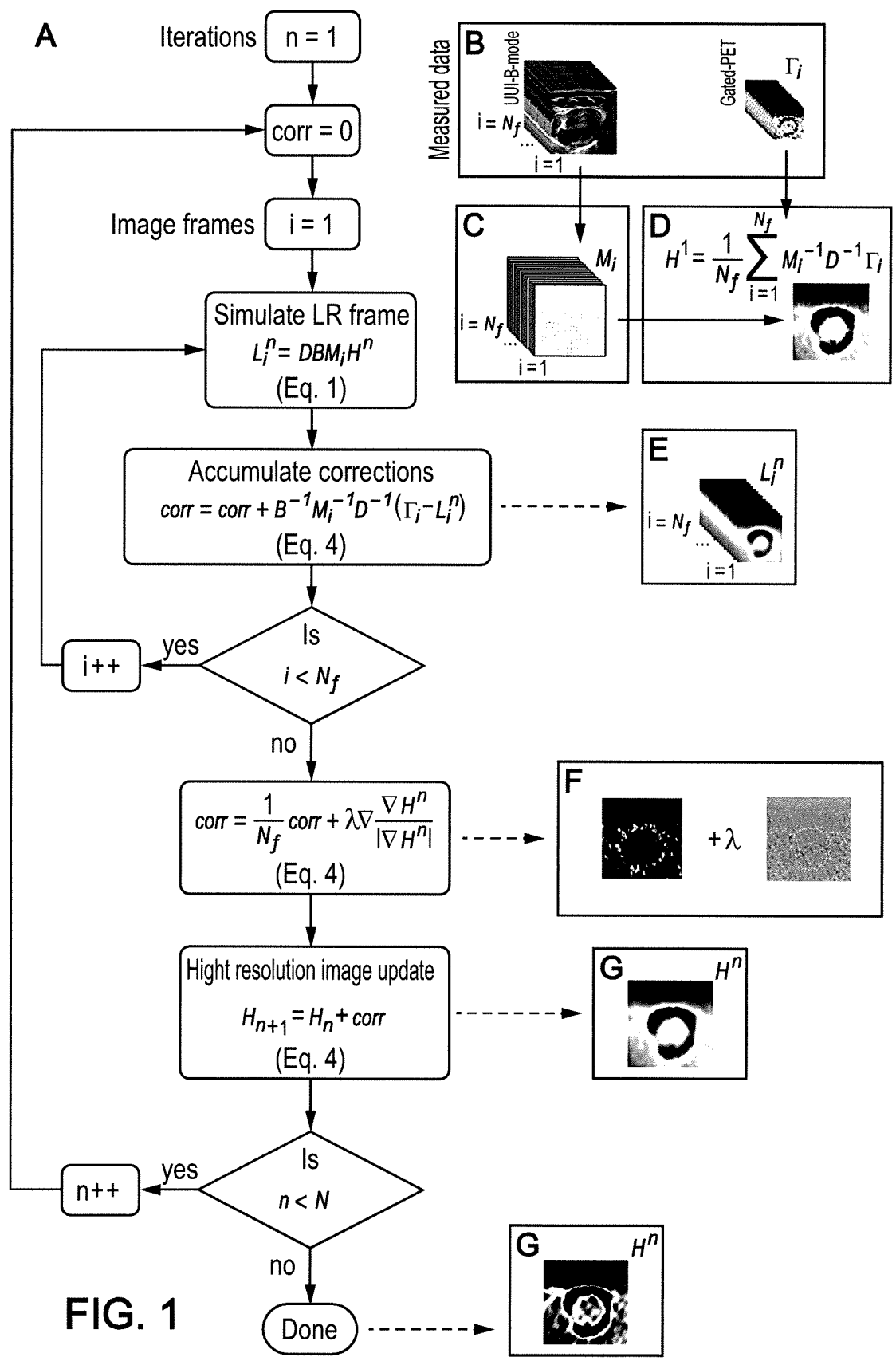
FIG. 1: A—schematic flow chart of the Ultrasound-based-SR method disclosed herein, to correct cardiac PET. B—multimodal PETRUS data simultaneously acquired and co-registered. C—UUI-B-mode estimated Motion Vector Fields of the heart's deformation. D—the initial high-resolution (HR) guess image used in the Ultrasound-based SR is the up-sampling of the result of registering and averaging all the low-resolution (LR) gated-PET frames. E—using Eq. 1 the HR image simulates LR frames. F—an averaged correction for the current HR image is calculated using Eq. 4 and regularized using TV, as shown in the last term of Eq. 4. G—HR image obtained at iterative step n of the algorithm. H—Final Ultrasound-based SR image.

SR restoration is an ill-conditioned problem since it aims to restore a high-resolution version of an object from a set of low-resolution images of it, that are related through a series of convolutional degrading steps such as motion, blurring, down-sampling and noise corruption:

$$L_i = DBM_i H + \Psi_i \qquad (1)$$

being H a high-resolution image of the inspected object, $L_i$ a set containing $i=1, \ldots, N_f$ low-resolution image frames of the object, $N_f$ is the total number of frames, $M_i$ the motion vector fields (MVF) containing the spatio-temporal geometrical transformation of the object motion at frame i, B a blurring kernel or point spread function (PSF) of the imaging system, D a down-sampling kernel defining the difference in pixel size between H and $L_i$ i.e. combining several voxels of the grid into one, for example using linear interpolation, and $\Psi_i$ an additive noise term.

$\Gamma_i$ is defined as being a dataset containing low-resolution frames of a Gated Cardiac-PET, such as successive time frames acquired synchronously with the electrocardiogram (ECG). Using $\Gamma_i$, a high-resolution original image is estimated:

$$H^* = \underset{H}{\operatorname{argmin}} \frac{1}{2} \sum_i |\Gamma_i - L_i^n|^2 + \lambda TV(H) \qquad (2)$$

where $L_i^n$ is a simulated set of low-resolution images that can be obtained through Eq. (1) using the high-resolution image $H^n$; $n=1, \ldots, N$ defines the iterations of the algorithm; $H^*$ is the optimal high-resolution image that solves the variational problem of Eq. (2); TV(H) is a penalizing function that measures the quality of the restored image by countering the effect of the noise term $\Psi_i$ and $\lambda$ is the regularization parameter that balances the weight of the penalization term.

Regarding the uptake FDG in the cardiac ventricular wall, a clear difference between healthy and injured tissue but very little variation of uptake inside the healthy tissue is expected. Hence, a Total Variation (TV) model as penalizing term has been adopted:

$$TV(H) = \int |\nabla H(r)| dr \qquad (3)$$

In Eq. (3), $\nabla$ denotes the gradient operator. To solve the Euler-Lagrange equation associated to the variational problem of Eq. (2), a steepest-descent algorithm has been used:

$$H^{n+1} = H^n + corr + \lambda \nabla \frac{\nabla H^n}{|\nabla H^n|}, \qquad (4)$$

-continued $$corr = \frac{1}{N_f} \sum_{i=1}^{N_f} B^{-1} M_i^{-1} D^{-1} (\Gamma_i - L_i^n).$$

In Eq. (4), $D^{-1}$ is the inverse of the down-sampling operator that performs the up-sampling of data, i.e. it divides each voxel of the grid in smaller voxels, $M_i^{-1}$ inverts the MVF (the approximation $M_i^{-1}=-M_i$ has been used) and the deblurring kernel $B^{-1}$ is the inverse of the blurring kernel B.

B. Super-Resolution in the Image Domain

The UUI-B-mode has been used in order to characterize the MVF, i.e. the $M_i$ term in Eq. (1.).

In the heart, this geometrical transformation matrix that is capable to align two given phases of the heart's motion is non-rigid as the pixels that contain heart tissue in an image move relatively independently from the pixels in close neighboring regions. Moreover, during the registration of ultrasound cardiac sequences, the ribs may induce dramatic attenuations of the signal intensity.

To account for the changes of intensity that might appear in ultrasonic sequences, both local and global image estimators have been combined by characterizing the local phase $\theta(x,y)$ and intensity of the image [23]. A distance metric derived from Demon-like registrations [26, 27] has been employed:

$$M_i = \frac{1}{2}\left[\frac{(I_R - I_{T_i})\nabla I_R}{\|\nabla I_R\|^2 + (I_R - I_{T_i})^2} + \frac{(\theta_R - \theta_{T_i})\nabla \theta_R}{\|\nabla \theta_R\|^2 + (\theta_R - \theta_{T_i})^2}\right] \quad (5)$$

wherein $I_{T_i}$ and $I_R$ are defined as the image template (at frame i) and reference, respectively; $\nabla$ is the gradient operator and $\theta_{T_i}$ and $\theta_R$ are the local phases of the image template and reference, respectively.

The local phase $\theta(x,y)$ can be obtained from the monogenic signal using quadrature filters, which are the combination of an even-symmetric band-pass filter ($F_e$, giving as result $I_e=F_e \otimes I$, the even component of an image I) and of two consecutive odd-symmetric filters ($F_{o1}$ and $F_{o2}$) applied to the even component of the signal:

$$\theta = \tan^{-1}\left(\frac{I_e}{\sqrt{(F_{01} \otimes I_e)^2 + (F_{02} \otimes I_e)^2}}\right) \quad (6)$$

A log-Garbor radial filter has been used as even filter and its Riesz transform as odd filters. Three uniformly decreasing center-frequency have been used for the band-pass for the log-Garbor filter, using 30, 20 and 10 pixels, which defines three consecutive scales. At each scale, 20 iterations were performed and the similarity function (Eq. (5)) has been evaluated using additive corrections. The final-scale motion field was regularized with a Gaussian low-pass kernel with Full-Width at Half-Maximum (FWHM) of 10 pixels.

C. Implementation Details for the Ultrasound-Based SR of Cardiac PET.

FIG. 1 A represents the flow-chart of the complete Ultrasound-based SR restoration problem for Cardiac-PET.

The algorithm is feed with the $\Gamma_i$ dataset of $N_f$ low-resolution Gated Cardiac-PET images and the co-registered UUI-B-mode $N_f$ frames (FIG. 1 B). The UUI-B-mode set, that have a smaller pixel size and a better spatial resolution than the PET, is used to estimate the geometrical transformation $M_i$ between frames (FIG. 1 C).

The algorithm starts with an initial high-resolution guess $H^1$, which is the image resulting from warping and averaging the $N_f$-Gated Cardiac-PET, up-sampled to the dimensions of the UUI-B-mode maps (FIG. 1 D). As in Eq. (1), $H^1$ is then (i) warped using each $M_i$, (ii) blurred and (iii), down-sampled to the dimensions of $\Gamma_i$, so as to produce $L^n_i$ (FIG. 1 E). The blurring kernel is the estimated Point Spread Function (PSF) of the PET scanner of PETRUS, previously characterized [9] as a Gaussian kernel with a FWHM of 1.5 mm at the center of the field-of-view. The deblurring kernel $B^{-1}$ should ideally be the inverse of the blurring kernel B. However, as the PSF of a PET scanner is generally represented as a Gaussian kernel, its exact inverse would lead to an ill-posed problem. Hence, a simple delta-function with a width of one pixel was used.

For all frames i, each difference ($\Gamma_i-L^n_i$) is up-sampled, warped-back to the selected frame of reference and averaged for all $N_f$. Using the current n estimation of the high-resolution image $H^n$, the divergence of the gradient of the TV term (last term in Eq. (4)) is calculated (FIG. 1 F) and, the n+1 estimation of the high-resolution image is obtained using Eq. (4).

To evaluate the gradient, border elements of the image are padded by replication outside the boundaries of the image. The regularization parameter $\lambda$ is empirically set to $1 \times 10^{-6}$ as it provided a satisfying tradeoff between noise control and spatial resolution in our experiments (see section of numerical experiments for details about the definitions of noise and spatial resolution used).

All these steps are reiterated until the root-mean-square-error (RMSE) between estimated and measured low-resolution images varies by less than 5% in two consecutive iterations.

D. PETRUS: Positron Emission Tomography Registered Ultrasonography

PETRUS has been described in detail in [24]. Briefly, it combines a preclinical PET-CT scanner for small animals (nanoScan Mediso Ltd., Hungary) with a clinical UUI scanner (Aixplorer, Supersonic Imagine France). The UUI component of PETRUS provides thousands of images per second, allowing the exploration of rapid phenomena with unprecedented spatial resolution (<100 μm).

Concerning cardiac studies in rats, PETRUS uses a commercial pediatric/rheumatology ultrasound probe (Super-Linear™ SLH20-6, Supersonic Imagine, France) with negligible effects on PET image quality [9]. The probe is attached through a 35 cm long hollow carbon rectangular cuboid (Polyplan Composites, France) to a six-degree-of-freedom high-precision micromotor (Hexapod H811, Physik Instrumente, Germany; minimum incremental motion 0.2 μm) fixed to the animal bed of the PET-CT scanner. A home-made 3D-printed plastic holder joins the carbon arm and the probe. Acoustic impedance coupling between the probe and the depilated skin of the animal is obtained using degassed ultrasound gel (Medi'gel Blue ECG, Drexco Medical).

Co-registration between UUI and PET requires accurate tracking of the ultrasound probe inside the PET gantry. The automatic process of multimodal data co-registration between UUI and PET volumes (detailed in [36]) provides a mean accuracy of co-registration of 0.10±0.03 mm. As a result, Ultrasound images and co-registered PET-CT images corresponding to the same space location are extracted.

In the present study the UUI-B-mode is used, typically with a plane FOV of 25.6 mm×(20 to 30) mm, a pixel-size of 0.1 mm×0.1 mm, and 16 temporal frames covering uniformly the full heart cycle.

Therefore, it is described herein an imaging method including:
a) acquiring N successive positron emission tomography (PET) low resolution images $\Gamma_i$ and simultaneously, N successive Ultrafast Ultrasound Imaging (UUI) images Ui of a moving object;
b) determining from each UUI image Ui, the motion vector fields $M_i$ that corresponds to the spatio-temporal geometrical transformation of the motion of the object;
c) obtaining a final estimated high resolution image H of the object by iterative determination of a high resolution image $H^{n+1}$ obtained by applying several correction iterations to a current estimated high resolution image $H^n$, n being the number of iterations, starting from an initial estimated high resolution image $H^1$ of the object, each correction iteration including at least:
  i) warping said estimated high resolution image $H^n$ using the motion vector fields $M_i$ to determine a set of low resolution reference images $L^n_i$;
  ii) determining a differential image Di by difference between each PET image $\Gamma_i$ and the corresponding low resolution reference image $L^n_i$;
  iii) warping back said differential images Di using the motion vector fields $M_i$ and averaging the N warped back differential images to obtain a high resolution differential image;
  iv) determining the high resolution image $H^{n+1}$ by correcting said high resolution image $H^n$ using said high resolution differential image;
d) applying the motion vector fields $M_i$ of each UUI image Ui to said final high resolution image H.

The method may further include one and/or other of the following features:
the motion vector fields $M_i$ of b) are estimated by combination of both global and local image estimators by characterizing respectively intensity and local phase information obtained from two consecutive frames of the set of UUI images;
the motion vector fields $M_i$ are estimated according to the following equation:

$$M_i = \frac{1}{2}\left[\frac{(I_R - I_{T_i})\nabla I_R}{\|\nabla I_R\|^2 + (I_R - I_{T_i})^2} + \frac{(\theta_R - \theta_{T_i})\nabla \theta_R}{\|\nabla \theta_R\|^2 + (\theta_R - \theta_{T_i})^2}\right]$$

wherein $I_{T_i}$ and $I_R$ are defined as the image template (at frame i) and reference, respectively; $\nabla$ is the gradient operator and $\theta_{T_i}$ and $\theta_R$ are the local phases of the image template and reference, respectively;
the local phase $\theta(x,y)$ is obtained from the monogenic signal using quadrature filters, which are the combination of an even-symmetric band-pass filter and of two consecutive odd-symmetric filters applied to the even component of the signal according to the following equation:

$$\theta = \tan^{-1}\left(\frac{I_e}{\sqrt{(F_{o1} \otimes I_e)^2 + (F_{o2} \otimes I_e)^2}}\right)$$

wherein $F_e$ is the even-symmetric band-pass filter, giving as result $I_e = F_e \otimes I$ being the even component of an image I, and wherein $F_{o1}$ and $F_{o2}$ are the odd-symmetric filters;
the even-symmetric band-pass filter is a log-Garbor radial filter and the two consecutive odd-symmetric filters correspond to the Riesz transform of the log-Garbor radial filter;
three uniformly decreasing center-frequency are used for the band-pass for the log-Garbor filter, using 30, 20 and 10 pixels, which defines three consecutive scales;
at each scale, 20 iterations are performed and the similarity function with each local phase scale is evaluated;
the final-scale motion field is regularized with a Gaussian low-pass kernel with a Full-Width at Half-Maximum of 10 pixels;
a) is performed using the UUI-B-mode dynamic sequence of the UUI system;
the initial estimated high resolution image $H^1$ of c) is obtained by up-sampling the image resulting from the motion registration of the N-frames gated-PET to the dimensions of the UUI-B-mode maps;
the positron emission tomography (PET) low resolution images $\Gamma_i$ are positron emission tomography-computed tomography (PET-CT) images;
in c) i), the low resolution reference images $L_i$ is estimated by down-sampling $H^n$ to the dimensions of the low-resolution images $\Gamma_i$, warping $H^n$ to a reference time frame i and blurring $H^n$ according to the following equation:

$$L^n_i = DBM_iH^n + \Psi_i,$$

wherein H is a high-resolution image of the inspected object, $L_i$ is a set containing i=1, . . . , $N_f$ low-resolution image frames of the object, $N_f$ is the total number of frames, $M_i$ is the motion vector fields (MVF) containing the spatio-temporal geometrical transformation of the object motion at frame i, B is a blurring kernel or point spread function (PSF) of the imaging system, D is a down-sampling kernel defining the difference in pixel size between H and $L_i$, i.e. combining several voxels of the grid into one, for example using linear interpolation, and $\Psi_i$ an additive noise term;
the n estimation $H^n$ of the high-resolution image is used to calculate the divergence of the gradient of the Total Variation (TV) model penalizing term, which measures the quality of the restored image by countering the effect of the noise term and which corresponds to the last term of the following equation, and wherein the n+1 estimation $H^{n+1}$ of the high-resolution image is obtained by means of the following steepest-descent algorithm $$H^{n+1} = H^n + corr + \lambda \nabla \frac{\nabla H^n}{|\nabla H^n|},$$

and
wherein the term corr is defined as follows $$corr = \frac{1}{N_f}\sum_{i=1}^{N_f} B^{-1}M_i^{-1}D^{-1}(\Gamma_i - L^n_i),$$

wherein $B^{-1}$ is a deblurring kernel being a delta function with a width of one pixel, $D^{-1}$ is the inverse of the down-sampling operator D that performs the up-sampling of data, $M_i^{-1}$ is the additive inverse of $M_i$, $\nabla$ denotes the gradient operator, and $\lambda$ is the regularization parameter that balances the weight of the penalization term;

the moving object to be imaged is an organ, preferably a living heart, more preferably a rodent living heart, even more preferably a human living heart.

Besides, it is also disclosed an imaging device comprising a positron emission tomography (PET) scanner, a Ultrafast Ultrasound Imaging (UUI) scanner and a processor, wherein said PET scanner acquire a set of N successive low resolution images $\Gamma_i$ and said UUI scanner simultaneously acquire a set of N successive images Ui of a moving object; and wherein the processor is configured to perform at least:

a) receiving the N successive positron emission tomography (PET) low resolution images $\Gamma_i$ and the simultaneously registered N successive Ultrafast Ultrasound Imaging (UUI) images Ui of said moving object;

b) determining from each UUI image Ui, the motion vector fields $M_i$ that corresponds to the spatio-temporal geometrical transformation of the motion of the object;

c) obtaining a final estimated high resolution image H of the object by iterative determination of a high resolution image $H^{n+1}$ obtained by applying several correction iterations to a current estimated high resolution image $H^n$, n being the number of iteration, starting from an initial estimated high resolution image $H^1$ of the object, each correction iteration including at least:

i) warping said estimated high resolution image $H^n$ using the motion vector fields $M_i$ to determine a set of low resolution reference images $L^n{}_i$;

ii) determining a differential image Di by difference between each PET image $\Gamma_i$ and the corresponding low resolution reference image $L^n{}_i$;

iii) warping back said differential images Di using the motion vector fields $M_i$ and averaging the N warped back differential images to obtain a high resolution differential image;

iv) determining the high resolution image $H^{n+1}$ by correcting said high resolution image $H^n$ using said high resolution differential image;

d) applying the motion vector fields $M_i$ of each UUI image Ui to said final high resolution image H.

The imaging device may further include one and/or other of the following features:

the PET scanner is a positron emission tomography-computed tomography (PET-CT) scanner;

the UUI scanner is configured to use the real-time B-mode imaging;

the UUI scanner comprises a transducer positioned over the moving object to be imaged by use of a motorized micropositioner and wherein the moving object to be imaged with the UUI transducer are positioned together inside the PET gantry;

the imaging device further comprises a remote control unit that control the motorized micropositioner, wherein the motorized micropositioner is a six-degrees-of-freedom motorized micropositioner and the control unit control the motorized micropositioner in programmed steps, for which the coordinates are expressed as a function of the PET system coordinates;

the moving object to be imaged is an organ, preferably a living heart, more preferably a rodent living heart, even more preferably a human living heart.

It is also disclosed a computer-readable medium comprising instructions which, when executed by a computer, cause the computer to carry out:

a) acquiring N successive positron emission tomography (PET) low resolution images $\Gamma_i$ and simultaneously, N successive Ultrafast Ultrasound Imaging (UUI) images Ui of a moving object;

b) determining from each UUI image Ui, the motion vector fields $M_i$ that corresponds to the spatio-temporal geometrical transformation of the motion of the object;

c) obtaining a final estimated high resolution image H of the object by iterative determination of a high resolution image $H^{n+1}$ obtained by applying several correction iterations to a current estimated high resolution image $H^n$, n being the number of iteration, starting from an initial estimated high resolution image $H^1$ of the object, each correction iteration including at least:

i) warping said estimated high resolution image $H^n$ using the motion vector fields $M_i$ to determine a set of low resolution reference images $L^n{}_i$;

ii) determining a differential image Di by difference between each PET image $\Gamma_i$ and the corresponding low resolution reference image $L^n{}_i$;

iii) warping back said differential images Di using the motion vector fields $M_i$ and averaging the N warped back differential images to obtain a high resolution differential image;

iv) determining the high resolution image $H^{n+1}$ by correcting said high resolution image $H^n$ using said high resolution differential image;

d) applying the motion vector fields $M_i$ of each UUI image Ui to said final high resolution image H.

EXPERIMENTS

The method was tested with numerical and animal data (n=2) acquired with the non-invasive hybrid imaging system PETRUS, that fuses PET, CT and UUI.

SNR, contrast, and spatial resolution of the treated images where measured and compared to the values obtained with static PET.

1. Numerical Experiment

The performance of the Ultrasound-based SR algorithm was tested on a numerical phantom simulating a realistic Gated Cardiac-PET acquisition in a numerical rat, using the ROBY phantom [12]. A total of 8 cardiac and 8 respiratory frames with 1-mm maximum diaphragm displacement were simulated to evaluate the impact of the cardiac and respiratory motions. The input images of the simulation consisted in 256×256×237 voxels of 0.4×0.4×0.4 mm covering the thoracic cage of the ROBY phantom. The phantom was simulated using the Monte Carlo software MCGPU-PET [32], a fast simulator which takes into account the main relevant physical processes of the emission, transport and detection of the radiation. A generic pre-clinical scanner model was used, with an associated spatial resolution at the center of the scanner of ~1.5 mm. Each simulation was based on the specific distribution of the activity and materials in each particular frame, and contained around 65 million counts, including trues and scatter coincidences. The acquired data of each frame were stored in 527 sinograms (direct and oblique), containing 129 and 168 radial and angular bins respectively. The simulated data were reconstructed with GFIRST [33], using a 3D-OSEM algorithm and including attenuation and scatter corrections. These corrections were obtained from the known material distribution in each frame, using a 2-tissues class segmentation (air and tissue). The images were reconstructed using 128×128×127 voxels of 0.8×0.8×0.746 mm. The whole simulation and reconstructions took in total ~52 minutes with a single GPU (GeForce GTX 1080, 1.73 GHz, 8 Gb).

The SR analysis was regionally limited to a single 2D slice in transversal orientation. The phantom activity information was used as anatomical reference to estimate the MVF, a down-sampling factor D of one every two pixels, and a Gaussian filter with FWHM of 1.5 mm as blurring kernel B. Mean pixels' values of regions of interest (ROIs) located in the left-ventricle wall and in the ventricle cavity were quantified. In order to simulate a static PET acquisition, the respiratory and cardiac frames of the reconstructed PET images were averaged. To simulate a Gated Cardiac-PET sequence, all the respiratory frames were averaged within each phase of the cardiac cycle. As the observed effect of respiration in the simulated Gated Cardiac-PET was a small rigid-translation in the cranio-caudal direction, a rigid registration was performed between the first frame of the reference anatomical image and the first frame of the simulated Gated Cardiac-PET before the registration of the cardiac phases. The estimated misfit was then applied to each frame of the Gated Cardiac-PET.

The improvement in image quality by the SR processing was assessed by measuring the Signal-to-Noise ratio (SNR), contrast and spatial resolution of the images. The SNR was calculated using the standard deviation (STD) and mean value (MEAN) in the ROIs as:

$$SNR(dB) = 10\log\left(\frac{MEAN}{STD}\right) \quad (7)$$

Contrast was defined as Weber's fraction [34] using the mean value in the left ventricle wall ROI ($MEAN_{wall}$) and in the cavity of the ventricle ROI ($MEAN_{cav}$).

$$Contrast = \frac{MEAN_{wall} - MEAN_{cav}}{MEAN_{cav}} \quad (8)$$

Spatial resolution was defined as the lateral spread function (LSF) of the ventricle's wall. This was evaluated as the FWHM of a Gaussian function fit to the mirrored duplicated points, external to the edge of the ventricle' wall, in a profile crossing the wall. The location of the external edge of the wall was extracted from the matching anatomical reference profile. The procedure was repeated on 5 intensity profiles drawn orthogonally to the heart wall, clockwise: basal lateral, mid lateral, apical, mid-septal and basal septal [35]. Resolution was then defined as the average of the five estimated LSF.

2. Animal Experiments

Figure 2:
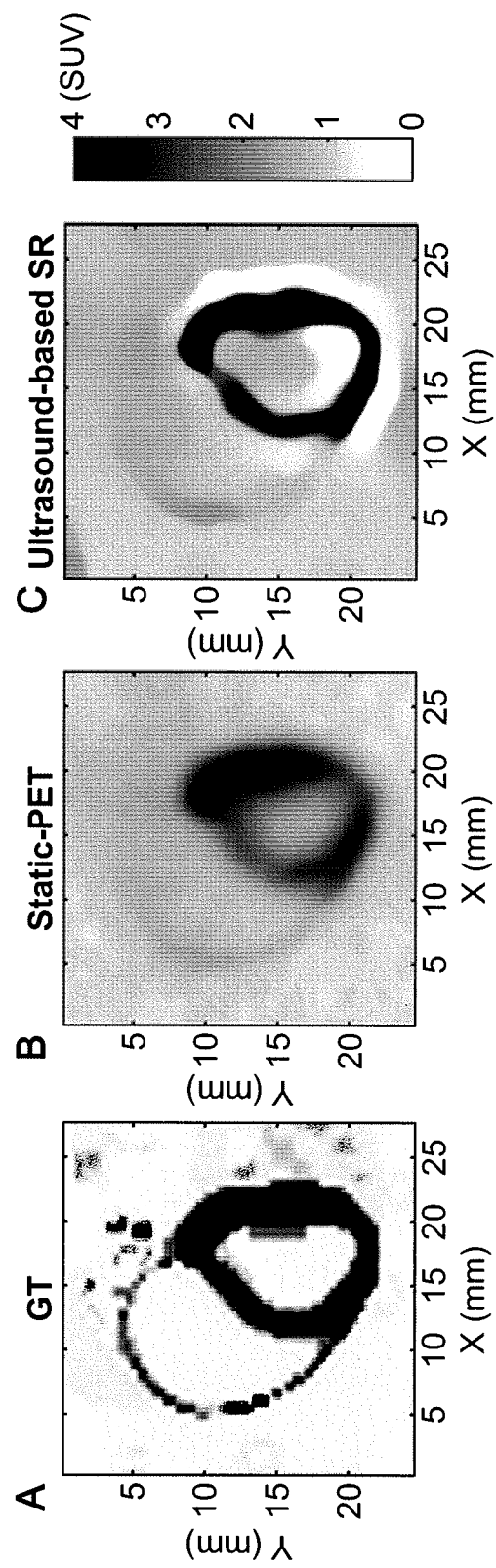
FIG. 2. Numerical test using PET simulated data with the realistic rat phantom including both respiratory and cardiac modeling (ROBY) and the Monte Carlo software MCGPU-PET. A—Ground-truth distribution of activity. B—Static-PET reconstruction. C—Ultrasound-based SR reconstruction.

Animal experiments were approved by the French Ethical Committee (approval number 18-146). Real data acquired with the PETRUS system from two successive imaging sessions of a 10-week-old female Wistar rat were processed: (i) in normal conditions (baseline) and (ii) after surgically-induced myocardial infarction. Baseline imaging was done 3 days before surgery. During surgery, the rat was under isoflurane anesthesia (2.5%) and physiological parameters were constantly monitored. Analgesics were injected before and post-surgery. A permanent ligation of the left anterior descending coronary artery (LADCA) was performed after thoracotomy under endotracheal intubation. The incision was sutured and the air in the thorax removed. The rat was imaged 4 hours after LADCA ligation. For both imaging sessions, the rat was positioned on a customized bed (as in FIG. 2 B) with ECG, temperature and respiration monitoring. A high level of isoflurane during anesthesia (~4%) was used in order to limit the respiratory rate and minimize the effect of respiratory motion on PET acquisitions. The ultrasound probe was positioned over the chest to obtain a standard long-axis view of the myocardium with B-mode-UUI at a frame-rate 500 fps during 5 seconds. UUI-B-mode acquisitions were triggered at the respiratory pause of the animal. A CT scan was acquired for attenuation correction of the PET data in semi-circular mode, with 50 kV, 720 projections, and 170 ms per projection. Attenuation correction was based on default settings of the PET-CT scanner using two tissues segmentation (tissue and air). Gated acquisition was started 30 minutes after the injection of 400 μL of ~41 MBq FDG in 0.9% NaCl. The 30-min ECG-Gated PET acquisition and UUI-B-mode were acquired simultaneously. From the sequence acquired with UUI-B-mode, a full cardiac cycle in respiratory pause was extracted using the simultaneously acquired ECG and respiratory signals. Next, the extracted frames were interpolated to 16 frames uniformly spaced in time. Every Gated Cardiac-PET image was reconstructed after removing heart cycles longer or shorter than 40% of the mean nominal heart cycle duration along the whole experiment. PET data were reconstructed using the Tera-Tomo reconstruction engine (Mediso, Hungary) with 6 iterations and 4 subsets, scatter and attenuation correction, and with 16 temporal frames, covering the full cardiac cycle. Finally, the multimodal PETRUS data was co-registered. A long-axis view was chosen in order to explore the territory irrigated by the LADCA.

RESULTS

Figure 3:
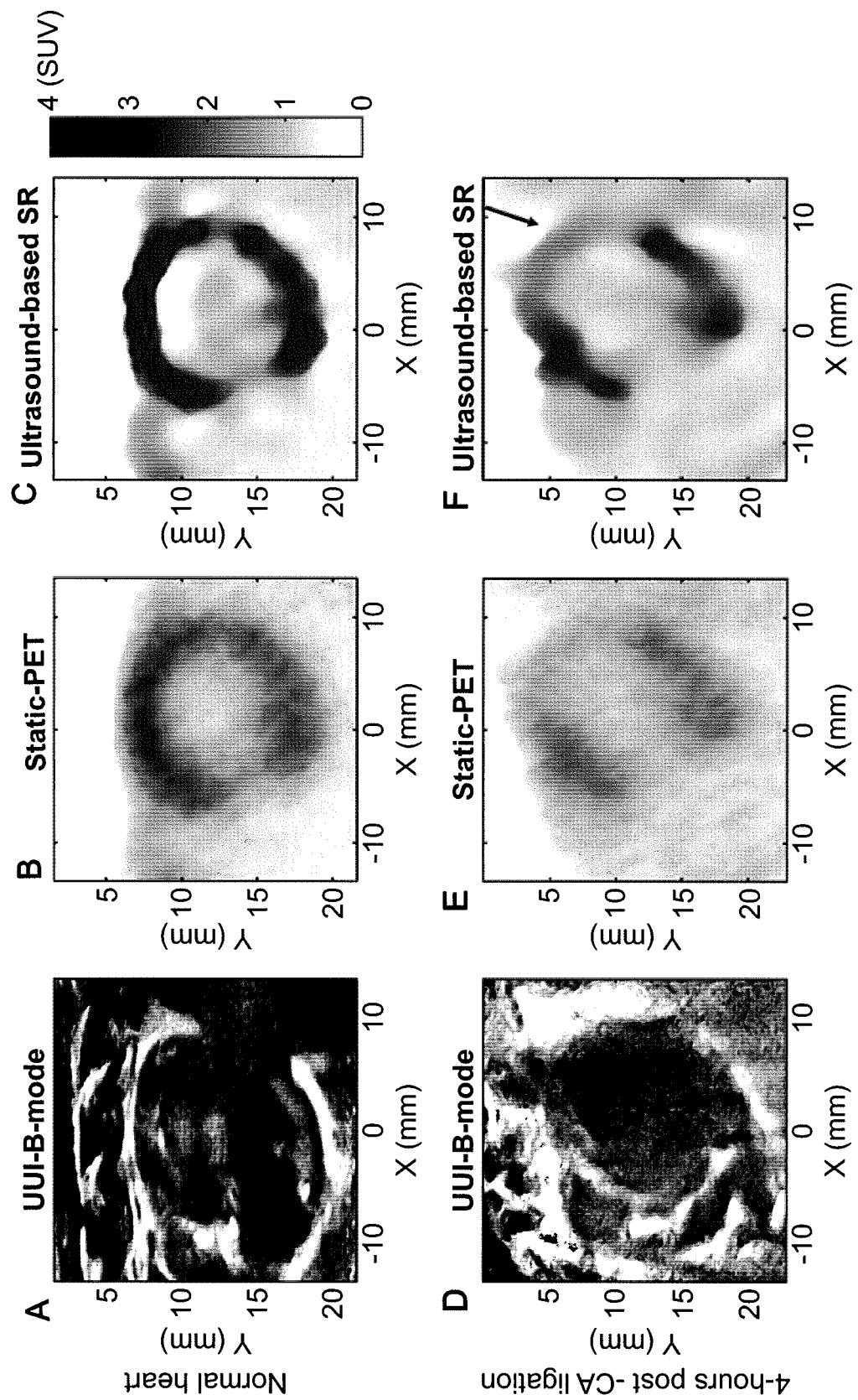
FIG. 3. Multimodal PETRUS images of an intact (A-C) and 4-hours post Left Anterior Descending Coronary Artery (LADCA) ligation (D-F) rat heart. A—UUI-B-mode image in long-axis orientation. B and E—Static-PET images. C and F—Ultrasound-based SR images. The black arrow in F points to the ischemic area.

FIG. 3 shows the results of the numerical tests comparing ground-truth, Static-PET, and Ultrasound-based SR images for the simulated PET experiment using the ROBY phantom. Compared to the reference image, image quality of the Static-PET image is notably degraded. The definition of the structure of the wall is partially lost as well as the quantitative information. However, the Ultrasound-based SR image is qualitatively and quantitatively improved in that respect. Quantification of the selected ROIs are reported in Table I. Ultrasound-based SR image was improved by 97% in the ventricular wall ROI and, by 60% in the central cavity of the ventricle, with respect to the static-PET image. Additionally, the Ultrasound-based SR image presented a 2 times higher contrast, a 21% better SNR and a 56% better spatial resolution than the static image.

FIG. 4 shows the UUI-B-mode, static-PET and Ultrasound-based SR images in intact and infarcted rat hearts and Table I reports their quantification. Qualitatively, in the Ultrasound-based SR images, the FDG uptake sharply delineated the walls of the left ventricle, with less spillover outside these tissues. SR clearly identified the metabolic remodeling in the ischemic myocardium corresponding to the vascular territory of the ligated LDACA.

Quantitatively, the mean FDG uptake in the different ROIs using Ultrasound-based SR increased in the regions of the walls and decreased in the cavity of the ventricle. In the case of the infarcted heart, Ultrasound-based SR shows better defined FDG distribution in the ventricle walls as well as a better delineation of the most affected regions after LADCA ligation. The mean contrast was twice higher than that of the static images, the SNR was improved by 30% and the spatial resolution by 56%, reaching a mean value of 0.88 mm.

Therefore, the results show that Ultrasound-based SR enhances the quality of PET images of the beating rodent heart: with respect to static PET, image contrast is improved by a factor of two, signal-to-noise ratio by 40% and spatial resolution by 56% (~0.88 mm). As a consequence, the metabolic defect following an acute cardiac ischemia was delineated with much higher anatomical precision.

The results support the view that Ultrasound-based SR improves the spatial resolution of the images without affecting the SNR. Analogously, all the image quality parameters evaluated were considerably improved, facilitating the identification of heart lesion, which appear enhanced in the images as a result of a better spatial resolution and decreased PVE. The total amount of counts present in the entire Gated sequence (2.35×10^10 and 2.63×10^10 counts for the intact and infarcted hearts, respectively) were not substantially modified by the Ultrasound-based SR algorithm (2.35×10$^{10}$ counts and 2.65×10$^{10}$ counts for the intact and infarcted heart). Importantly, the ultrasound image acquisition is performed during the PET acquisition and provides images in real time. Co-registration of multimodal data takes 2 minutes on a dual core Intel® Xeon® CPU E-5-2637 v4 @ 3.5 GHz, and most of this time is used for data loading of the PET volumes. Ultrasound-based SR adds a short computation time to the reconstruction process. The motion registration of 16 UUI-B-mode frames takes 4 minutes, and the SR algorithm 1 minute on the same machine. Both codes were run in non-parallelized conditions, while parallelization is likely to improve considerably the execution time.

TABLE I

QUANTITATIVE ANALISIS OF TREATED IMAGES

| | ROI | Static | U-based SR |
|---|---|---|---|
| | Numerical experiments | | |
| | Wall (SUV = 4) | 3.32 ± 0.17 | 4.02 ± 0.11 |
| | Cav. (SUV = 1) | 1.57 ± 0.19 | 1.23 ± 0.14 |
| | Contrast (ad) | 1.11 | 2.27 |
| | SNR (dB) | 12.91 | 15.63 |
| | S. Res. (mm) | 1.89 | 0.84 |
| | Animal experiments | | |
| BL | Wall | 3.63 ± 0.21 | 4.27 ± 0.11 |
| | Cav. | 1.33 ± 0.11 | 1.01 ± 0.13 |
| | Contrast (ad) | 1.73 | 3.23 |
| | SNR (dB) | 12.38 | 15.89 |
| | S. Res. (mm) | 1.99 | 0.85 |
| I | Wall | 2.80 ± 0.20 | 3.88 ± 0.12 |
| | Cav. | 1.37 ± 0.26 | 1.15 ± 0.14 |
| | Lesion | 1.56 ± 0.15 | 2.18 ± 0.17 |
| | Contrast (ad) | 1.04 | 2.37 |
| | SNR (dB) | 11.46 | 15.10 |
| | S. Res. (mm) | 2.01 | 0.90 |

I: Infarcted; BL: Baseline; Static: Static PET; U-based SR: Super-Resolution based on Ultrasound; Wall: ventricle's wall; Cav: cavity inside ventricle; Lesion: ischemic area

The invention claimed is:

1. An imaging method including:
   a) acquiring N successive positron emission tomography (PET) low resolution images $\Gamma_i$ and simultaneously, N successive Ultrafast Ultrasound Imaging (UUI) images Ui of a moving object;
   b) determining from each UUI image Ui, the motion vector fields $M_i$ that corresponds to the spatio-temporal geometrical transformation of the motion of the object;
   c) obtaining a final estimated high resolution image H of the object by iterative determination of a high resolution image $H^{n+1}$ obtained by applying several correction iterations to a current estimated high resolution image $H^n$, n being the number of iterations, starting from an initial estimated high resolution image $H^1$ of the object, each correction iteration including at least:
   i) warping said estimated high resolution image $H^n$ using the motion vector fields $M_i$ to determine a set of low resolution reference images $L^n_i$;
   ii) determining a differential image Di by difference between each PET image $\Gamma_i$ and the corresponding low resolution reference image $L^n_i$;
   iii) warping back said differential images Di using the motion vector fields $M_i$ and averaging the N warped back differential images to obtain a high resolution differential image;
   iv) determining the high resolution image $H^{n+1}$ by correcting said high resolution image $H^n$ using said high resolution differential image;
   d) applying the motion vector fields $M_i$ of each UUI image Ui to said final high resolution image H.

2. The imaging method according to claim 1, wherein the motion vector fields $M_i$ of b) are estimated by combination of both global and local image estimators by characterizing respectively intensity and local phase information obtained from two consecutive frames of the set of UUI images.

3. The imaging method according to claim 2, wherein the motion vector fields $M_i$ are estimated according to the following equation:

$$M_i = \frac{1}{2}\left[\frac{(I_R - I_{T_i})\nabla I_R}{\|\nabla I_R\|^2 + (I_R - I_{T_i})^2} + \frac{(\theta_R - \theta_{T_i})\nabla\theta_R}{\|\nabla\theta_R\|^2 + (\theta_R - \theta_{T_i})^2}\right]$$

wherein $I_{T_i}$ and $I_R$ are defined as the image template (at frame i) and reference, respectively; $\nabla$ is the gradient operator and $\theta_{T_i}$ and $\theta_R$ are the local phases of the image template and reference, respectively.

4. The imaging method according to claim 2, wherein the local phase $\theta(x,y)$ is obtained from the monogenic signal using quadrature filters, which are the combination of an even-symmetric band-pass filter and of two consecutive odd-symmetric filters applied to the even component of the signal according to the following equation:

$$\theta = \tan^{-1}\left(\frac{I_e}{\sqrt{(F_{o1} \otimes I_e)^2 + (F_{o2} \otimes I_e)^2}}\right)$$

wherein $F_e$ is the even-symmetric band-pass filter, giving as result $I_e = F_e \otimes I$ being the even component of an image I, and wherein $F_{o1}$ and $F_{o2}$ are the odd-symmetric filters.

5. The imaging method according to claim 4, wherein the even-symmetric band-pass filter is a log-Garbor radial filter, the two consecutive odd-symmetric filters correspond to the Riesz transform of the log-Garbor radial filter, wherein three uniformly decreasing center-frequency are used for the band-pass for the log-Garbor filter, using 30, 20 and 10 pixels, which defines three consecutive scales, wherein at each scale, 20 iterations are performed and the similarity function with each local phase scale is evaluated, and wherein the final-scale motion field is regularized with a Gaussian low-pass kernel with a Full-Width at Half-Maximum of 10 pixels.

6. The imaging method according to claim 1, wherein a) is performed using the UUI-B-mode dynamic sequence of the UUI system and wherein the initial estimated high resolution image $H^1$ of c) is obtained by up-sampling the image resulting from the motion registration of the N-frames gated-PET to the dimensions of the UUI-B-mode maps.

7. The imaging method according to claim 1, wherein the positron emission tomography (PET) low resolution images $\Gamma_i$ are positron emission tomography-computed tomography (PET-CT) images.

8. The imaging method according to claim 1, wherein in c) i), the low resolution reference images $L_i$ is estimated by down-sampling $H^n$ to the dimensions of the low-resolution images $\Gamma_i$, warping $H^n$ to a reference time frame i and blurring $H^n$ according to the following equation:

$$L^n_i = DBM_i H^n + \Psi_i,$$

wherein H is a high-resolution image of the inspected object, $L_i$ is a set containing i=1, ..., $N_f$ low-resolution image frames of the object, $N_f$ is the total number of frames, $M_i$ is the motion vector fields (MVF) containing the spatio-temporal geometrical transformation of the object motion at frame i, B is a blurring kernel or point spread function (PSF) of the imaging system, D is a down-sampling kernel defining the difference in pixel size between H and $L_i$, by combining several voxels of the grid into one, for example using linear interpolation, and $\Psi_i$ an additive noise term.

9. The method of claim 8, wherein the combining of several voxels is performed using linear interpolation and $\Psi_i$ an additive noise term.

10. The imaging method according to claim 1, wherein the n estimation $H^n$ of the high-resolution image is used to calculate the divergence of the gradient of the Total Variation (TV) model penalizing term, which measures the quality of the restored image by countering the effect of the noise term and which corresponds to the last term of the following equation, and wherein the n+1 estimation $H^{n+1}$ of the high-resolution image is obtained by means of the following steepest-descent algorithm $$H^{n+1} = H^n + corr + \lambda \nabla \frac{\nabla H^n}{|\nabla H^n|},$$

and wherein the term corr is defined as follows $$corr = \frac{1}{N_f} \sum_{i=1}^{N_f} B^{-1} M_i^{-1} D^{-1} (\Gamma_i - L_i^n),$$

wherein $B^{-1}$ is a deblurring kernel being a delta function with a width of one pixel, $D^{-1}$ is the inverse of the down-sampling operator D that performs the up-sampling of data, $M_i^{-1}$ is the additive inverse of $M_i$, $\nabla$ denotes the gradient operator, and $\lambda$ is the regularization parameter that balances the weight of the penalization term.

11. The imaging method according to claim 1, wherein the moving object to be imaged is an organ.

12. The imaging method according to claim 11, wherein the organ is a living heart.

13. The imaging method according to claim 12, wherein the living heart is in a closed-chest.

14. The imaging method according to claim 13, wherein the living heart is a rodent living heart.

15. The imaging method according to claim 13, wherein the living heart is a human living heart.

16. An imaging device comprising a positron emission tomography (PET) scanner, a Ultrafast Ultrasound Imaging (UUI) scanner and a processor, wherein said PET scanner acquires a set of N successive low resolution images $\Gamma_i$ and said UUI scanner simultaneously acquires a set of N successive images Ui of a moving object; and wherein the processor is configured to perform at least:

a) receiving the N successive positron emission tomography (PET) low resolution images $\Gamma_i$ and the simultaneously registered N successive Ultrafast Ultrasound Imaging (UUI) images Ui of said moving object;

b) determining from each UUI image Ui, the motion vector fields $M_i$ that correspond to the spatio-temporal geometrical transformation of the motion of the object;

c) obtaining a final estimated high resolution image H of the object by iterative determination of a high resolution image $H^{n+1}$ obtained by applying several correction iterations to a current estimated high resolution image $H^n$, n being the number of iteration, starting from an initial estimated high resolution image $H^1$ of the object, each correction iteration including at least:

i) warping said estimated high resolution image $H^n$ using the motion vector fields $M_i$ to determine a set of low resolution reference images $L^n_i$;

ii) determining a differential image Di by difference between each PET image $\Gamma_i$ and the corresponding low resolution reference image $L^n_i$;

iii) warping back said differential images Di using the motion vector fields $M_i$ and averaging the N warped back differential images to obtain a high resolution differential image;

iv) determining the high resolution image $H_{n+1}$ by correcting said high resolution image $H_n$ using said high resolution differential image;

d) applying the motion vector fields $M_i$ of each UUI image Ui to said final high resolution image H.

17. The imaging device according to claim 16, wherein the PET scanner is a positron emission tomography-computed tomography (PET-CT) scanner and wherein the UUI scanner is configured to use the real-time B-mode imaging.

18. The imaging device according to claim 16, wherein the UUI scanner comprises a transducer positioned over the moving object to be imaged by use of a motorized micropositioner and wherein the moving object to be imaged with the UUI transducer are positioned together inside the PET gantry.

19. The imaging device according to claim 16, further comprising a remote control unit that control the motorized micropositioner, wherein the motorized micropositioner is a six-degrees-of-freedom motorized micropositioner and the control unit controls the motorized micropositioner in programmed steps.

20. A non-transitory computer-readable medium comprising instructions which, when executed by a computer, cause the computer to carry out:
- a) acquiring N successive positron emission tomography (PET) low resolution images $\Gamma_i$ and simultaneously, N successive Ultrafast Ultrasound Imaging (UUI) images Ui of a moving object;
- b) determining from each UUI image Ui, the motion vector fields $M_i$ that corresponds to the spatio-temporal geometrical transformation of the motion of the object;
- c) obtaining a final estimated high resolution image H of the object by iterative determination of a high resolution image $H^{n+1}$ obtained by applying several correction iterations to a current estimated high resolution image $H^n$, n being the number of iteration, starting from an initial estimated high resolution image $H^1$ of the object, each correction iteration including at least:
  - i) warping said estimated high resolution image $H^n$ using the motion vector fields $M_i$ to determine a set of low resolution reference images $L''_i$;
  - ii) determining a differential image Di by difference between each PET image $\Gamma_i$ and the corresponding low resolution reference image $L''_i$;
  - iii) warping back said differential images Di using the motion vector fields $M_i$ and averaging the N warped back differential images to obtain a high resolution differential image;
  - iv) determining the high resolution image $H^{n+1}$ by correcting said high resolution image $H^n$ using said high resolution differential image;
- d) applying the motion vector fields $M_i$ of each UUI image Ui to said final high resolution image H.

* * * * *